United States Patent [19]

Claytor et al.

[11] Patent Number: 4,696,191

[45] Date of Patent: Sep. 29, 1987

[54] APPARATUS AND METHOD FOR VOID/PARTICULATE DETECTION

[75] Inventors: Thomas N. Claytor, Woodridge, Ill.; Carl E. Ockert, Vienna, Va.; Richard Randall, Canoga Park, Calif.

[73] Assignee: The United States of America as represented by the United States Department of Energy, Washington, D.C.

[21] Appl. No.: 877,959

[22] Filed: Jun. 24, 1986

[51] Int. Cl.[4] .............................. G01N 29/04
[52] U.S. Cl. ............................ 73/600; 73/19
[58] Field of Search .................. 73/600, 19, 599, 579, 73/865.5

[56] References Cited

U.S. PATENT DOCUMENTS

| 3,529,234 | 9/1970 | Keen . | |
|---|---|---|---|
| 3,738,154 | 6/1973 | Henry . | |
| 3,744,301 | 7/1973 | Arave . | |
| 3,830,095 | 8/1974 | Jaross . | |
| 3,973,152 | 8/1976 | Karplus . | |
| 3,974,681 | 8/1976 | Namery .............................. | 73/19 |
| 4,112,735 | 9/1978 | McKnight . | |
| 4,144,741 | 3/1979 | Nakamoto . | |
| 4,235,095 | 11/1980 | Liebermann . | |
| 4,392,374 | 7/1983 | Liebermann . | |
| 4,542,644 | 9/1985 | Claytor et al. ..................... | 73/599 |
| 4,567,749 | 2/1986 | Amblard et al. ................... | 73/599 |
| 4,607,520 | 8/1986 | Dam .................................. | 73/19 |

OTHER PUBLICATIONS

ANL-84-96, "Passive Acoustic Imaging: Steam Generator Test Results" by Thomas N. Claytor et al.
Kinsler et al., "Fundamentals of Acoustics", pp. 228-230.
ANL-82-60, "Void/Particulate Monitor Tests at EBR-II" by Thomas N. Claytor.

Primary Examiner—Anthony V. Ciarlante
Attorney, Agent, or Firm—Hugh W. Glenn; Robert J. Fisher; Judson R. Hightower

[57] ABSTRACT

Apparatus and method for detecting voids and particulates in a fluid within a containing vessel. A diffuse ultrasonic signal is coupled into the fluid by a first transducer and the portion of the ultrasonic signal transmitted through the fluid is detected by a second transducer. The received signal is analyzed by a processor to determine the void fraction of the fluid responsive to the attenuation of the received ultrasonic signal. In addition, voids and particulates are detected by evaluating the increase in side-band energy of the received signal.

23 Claims, 6 Drawing Figures

APPARATUS AND METHOD FOR VOID/PARTICULATE DETECTION

CONTRACTUAL ORIGIN OF THE INVENTION

The United States has rights in this invention pursuant to Contract No. W-31-109-ENG-38 between the United States Department of Energy and Argonne National Laboratory.

BACKGROUND OF THE INVENTION

This invention relates generally to the detection of voids or particulates in a fluid and more particularly to novel method and apparatus for detecting voids or particulates in a fluid by measuring the attenuation and doppler shift of a diffuse ultrasonic sound field passed through the fluid containing the voids.

The detection of voids in the fluid in pipes or containing vessels such as steam generators is important in various industries where the control of fluid levels and the detection of leaks is crucial. For example, in the nuclear reactor industry, high pressure water is contained in opaque steel pipes which must remain full of water to provide coolant to the reactor core. The presents of voids in the coolant could be an indication of a large leak, a low water level, low water pressure or an over power condition in the reactor core. Also, in large volume chemical processing systems in chemical plants it is sometimes desirable to be able to monitor voids to ensure proper operation. It is thus desirable to have a means to monitor the amount of voids in a pipe or other containing vessel by direct measurement rather than by inference through some other less direct measurement means.

The invention is particularly useful for detecting voids in the liquid metal coolant (e.g., sodium) of a fast breeder reactor. Although sodium has many advantages as a coolant, it is unfortunately opaque and very chemically reactive. When steam in a breeder reactor steam generator leaks into the sodium, the resultant reaction is exothermic and produces hydrogen bubbles and other reaction products. The hydrogen gas may however eventually dissolve in the sodium before the voids can be detected by prior art means of detection.

The principle prior art leak detection technique for detecting water leaks into sodium detects the presents of hydrogen dissolved in sodium. Hydrogen is detected by the diffusion of the hydrogen through a thin nickel membrane immersed in the sodium. This technique is a sensitive detector for steam/water leaks but has several deficiencies. Since the hydrogen detector is immersed in sodium it is not easy to replace and is very costly. This type of hydrogen meter is usually located some distance away from the steam generator/heat exchanger and therefore the sodium must be transported to the detector by sodium flow. At low sodium flow rates and because of hydrogen diffusion time through the nickel membrane, the response time of the hydrogen meter is slow. Finally, the technique does not distinguish leaked hydrogen from extraneous hydrogen which may be present in the system after tube cleaning or during initial operation.

Another prior art means of leak detection is based on the acoustic noise emitted by high pressure water or steam flow as it issues from a small hole or crack. This technique is sensitive to background acoustic noise level changes due to flow noise. Because of this limitation, very high sodium and steam flow rates render this detection means less sensitive.

A prior art method to detect voids and particulates in the flow stream of the outlet line of a steam generator has been proposed which detects back scattering of an ultrasonic beam due to the flow of voids passed the outlet. However, because of high temperatures in the sodium of the steam generator/heat exchanger some of the voids and particulates may dissolve before reaching the outlet line. Also at low sodium flow rates, the voids may not be entrained in the sodum flow. Consequently it is desirable to have a detector that is rapid, nonintrusive, low cost, easily replaceable and reliable.

It is accordingly an object of this invention to provide an improved method and apparatus to detect voids and particulates in pipes as well as complex structures such as steam generators and heat exchangers.

It is another object of the present invention to provide a method and apparatus that detects voids in the fluid in a steam generator regardless of the fluid flow rates.

It is yet another object of the invention to provide an improved method and apparatus to detect voids and particulates in a fluid by detecting attenuation of an ultrasonic signal coupled into the fluid.

It is yet another object of the invention to provide a novel method and apparatus for improving the safety of operation of a steam generator by means of cost effective, reliable and rapid detection of leaks.

Briefly, according to the foregoing and other objects and acording to one embodiment of the invention, apparatus for detecting voids and particulates in a fluid within a containing means is provided comprising first transducer means coupled to a first location on the containing means for transmitting a diffuse ultrasonic sound field of predetermined frequency into the fluid. In addition, second transducer means is coupled to a second location on the containing means for receiving a portion of the transmitted sound field and generating an electrical signal representative of the received sound field. A signal processing means coupled to the second transducer means is provided for processing the electrical signals to determine the presence of voids and particulates responsive to attenuation of the sound field transmitted through the fluid.

BRIEF DESCRIPTION OF THE DRAWINGS

The invention, together with further objects and advantages thereof, may be understood by reference to the following description taken in conjunction with the accompanying drawings.

DETAILED DESCRIPTION OF THE PREFERRED EMBODIMENT

Figure 1:
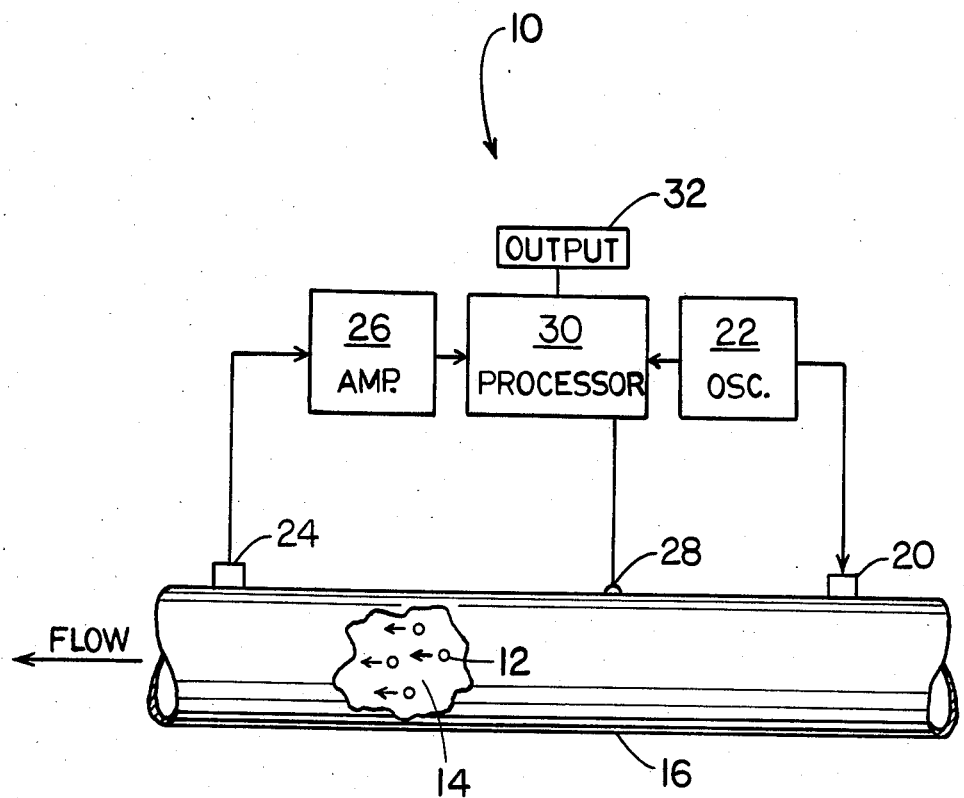
FIG. 1 is a generalized block diagram illustrating a specific embodiment of a pipe mounted void/particulate detector according to the invention.

FIG. 1 is a generalized block diagram illustrating a void/particulate detector 10 according to the invention. Voids (e.g. vapor bubbles) or particulates 12 in the fluid 14 within a containing vessel 16 (e.g. pipe in the illustrated embodiment) are detected by measuring the absorption of diffuse transmitted acoustic energy (e.g. ultrasonic energy where the frequency exceeds 20 khz in the illustrated embodiment) transmitted by a transmitting transducer 20 (e.g. a piezoelectric ceramic transducer such as a Acoustic Emission Technology, Inc., Model 375).

The use of a diffuse ultrasonic signal as well as transmission generally in or against the direction of fluid flow or along the axial direction of the pipe 16 permits the whole length of the pipe or containing vessel 16 to be interrogated for voids. Further, the invention avoids the need for the fluid to flow past the sensors and permits the use of small and easily replaceable sensors. The use of a diffuse sound field also permits detection of voids in containing vessels with complex geometries such as bends, pipe transitions, tees, baffle plates, etc. Thus, by coupling the ultrasonic sound signal into the pipe wall or into a large element of steam generator or other fluid containing vessel, the signal enters the fluid as a diffuse sound field which can travel around and through baffle plates or other complex geometries before reaching the receiving transducer 24. In addition, while transmission may be across the vessel and across the fluid flow, it may be desirable in many cases for the diffuse sound field to be transmitted along the axis of fluid flow.

Figure 4A:
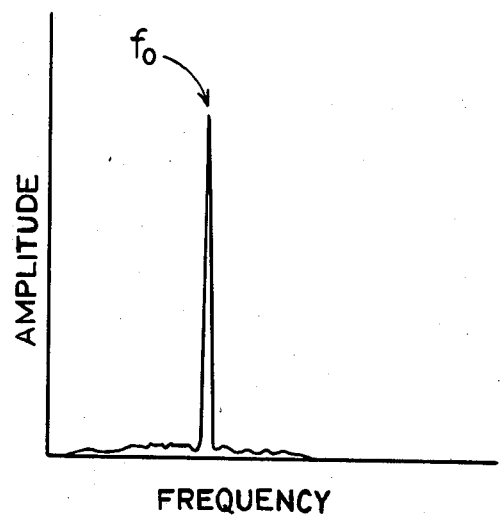
FIG. 4A is a frequency versus amplitude plot of the output of the transmitting transducer of FIGS. 1 and 2.

Transducer 20 converts an electrical sine wave signal of predetermined center frequency $f_0$ generated by an oscillator 22 to an acoustic signal which is coupled into the fluid as a diffuse sound field. The signal coupled into the fluid, in the illustrated embodiment, comprises a narrow band of frequencies centered on a predetermined center frequency $f_0$ having a frequency distribution such as that shown in the frequency vs. amplitude plot of FIG. 4A.

The transmitting transducer 20 and the receiving transducer 24 (i.e. detector) may be coupled to the pipe by a variety of means such as direct contact to the pipe 16, a waveguide, etc. The receiving transducer 24 is coupled to the pipe 16 at a location which, in the illustrated embodiment, is down (or up) stream from the transmitting transducer 20. The receiving transducer 24 detects the signals that are transmitted along the pipe wall and also the signals that have been transmitted through the fluid 14. Attenuation in the fluid 14 is less than that in the pipe wall when the distance between the transmitting transducer 20 and the receiving transducer 24 is large (e.g. in the illustrated embodiment, approx. 1 to 20 meters). Therefore, the ultrasonic signal detected by the receiving transducer 24 under these conditions will primarily be due to the ultrasonic signal energy which is traveling through the fluid.

At the resonance frequency of a bubble, a small number of bubbles can cause a large attenuation thereby permitting a very sensitive system for void detection. Resonance occurs at those acoustic frequencies given by the equation $f_o = (\frac{1}{2}\pi a)(3\gamma P_o/\rho)^{\frac{1}{2}}$ where a = the radius of bubble, $\gamma$ is the specific heat of the gas in the bubble, $P_o$ is the external fluid pressure, and $\rho$ is the density of the fluid. Thus, the frequency of operation of the illustrated embodiments of the invention is chosen so that the background noise from the pipe or steam generator is small in comparison to the received signal yet attenuation due to the bubbles is large due to resonance. In addition, the frequency of operation is chosen to permit the signal to be propagated over a sufficient distance to interrogate the desired volume since high frequency signals attenuate faster. These objectives can be achieved in the illustrated embodiments by operating the invention in a range of frequencies below approximately 500 khz.

The ultrasonic signal detected by the transducer 24 is converted by the transducer 24 to an electrical signal and coupled, as shown, to an amplifier 26. Amplifier 26 amplifies the electrical signal from the transducer 24 and couples the amplified signal to a signal processor 30, as shown. Also coupled to the signal processor 30 is the sine wave signal output of the oscillator 22 and the output of a temperature sensor 28 (e.g. a thermocouple). The temperature sensor 28 generates an electrical output signal representative of the temperature of the fluid 14.

Figure 4B:
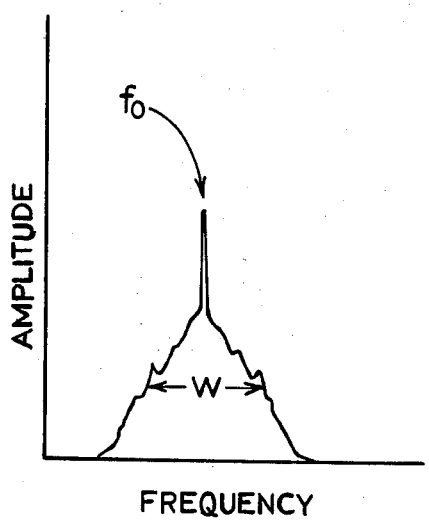
FIG. 4B is a frequency versus amplitude plot of the signal received by the receiving transducer of FIGS. 1 and 2 when voids are present in the fluid.
Figure 4C:
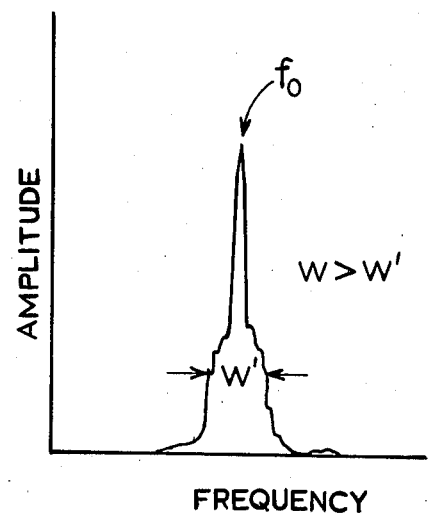
FIG. 4C is a frequency versus amplitude plot of the signal received by the receiving transducer of FIGS. 1 and 2 when no voids are present.

The signal processor 30 processes the received ultrasonic signal using the output of the oscillator 22 as a reference and using the temperature signal from the sensor 28 to evaluate the attenuation of the signal transmitted through the fluid 14 and received by the transducer 24. A typical received signal will have a general frequency distribution similar to that shown in the amplitude vs. frequency plot of FIG. 4B when voids are present in the fluid. If no voids are present, the received signal will be more like that of FIG. 4C. A comparison with FIG. 4B illustrates that the amplitude of the center frequency component is much less attenuated than when voids are present and the sidebands are narrower (i.e. $w > w'$). Since voids attenuate sound waves in a fluid and only a small void fraction (where void fraction is defined as the volume of the voids divided by the total fluid volume) is necessary to cause a measurable absorption of the signal, processor 30 can determine the void fraction (or presence of particulates) of the fluid based upon the signal attenuation. In addition the signal processor 30 may analyze side-band energy produced by the motion of voids and particulates to detect such voids and particulates in the fluid. Upon determining a degree of attenuation or void fraction or upon determining that the void fraction exceed a threshold, the signal processor 30 outputs a signal to an operator on output device 22. The output device 22 may be one of or a combination of a variety of devices, such as a visual or audible alarm, a printer, a real time digital display of void fraction, etc.

Figure 2:
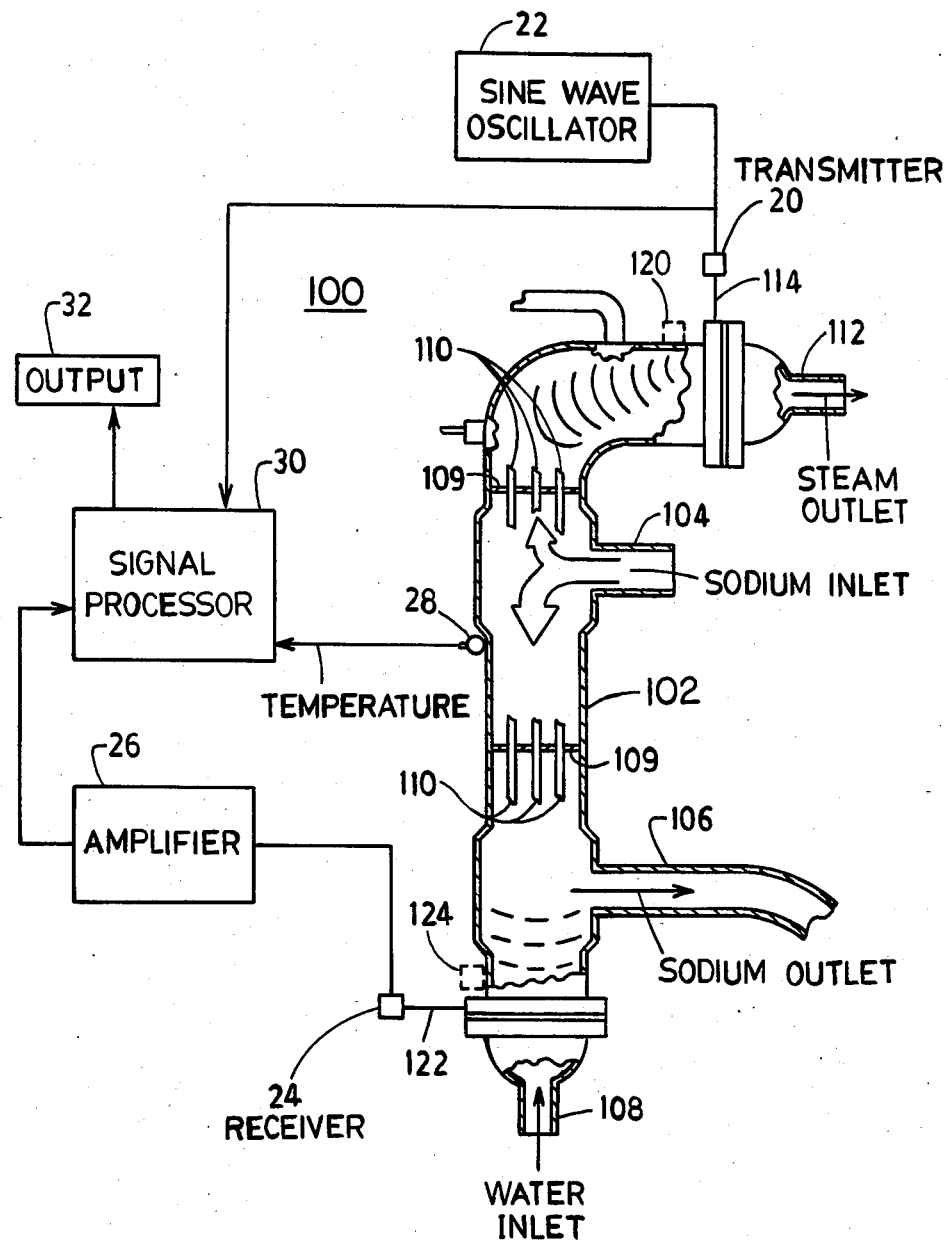
FIG. 2 is a generalized block diagram illusrating a specific embodiment of a steam generator mounted void/particulate detector according to the invention.

Referring now to FIG. 2, there is shown a block diagram illustrating a specific embodiment of a steam generator mounted void/particulate detector 100. A steam generator 102, such as are utilized in fast breeder nuclear reactors, functions as a heat exchanger in which molten sodium from the reactor (not shown) enters at a sodium inlet 104 and exits via an outlet 106 after passing over baffle plates 109 and tube bundles 110, as shown. Water to be heated enters through a water inlet 108 and circulates through conventional steam generator tube bundles 110 to absorb heat from the molten sodium. The heated water (steam) exits the steam generator via a steam outlet 112 to power a set of turbines (not shown). In such a steam generator 102, a leak of water into the sodium will result in a reaction creating hydrogen bubbles (voids) and sodium oxide in the fluid. It is crucial that such a dangerous condition be detected as soon as possible. However, the complex geometry of the system including tube bundles, bends, changes in vessel diameter, etc., make rapid, reliable detection of the void very difficult using prior art techniques. The use of this technique with other methods provides a reliable detection system.

In the illustrated embodiment of FIG. 2, the transmitting transducer 20 is coupled to the tube sheet of the steam generator 102 or near the steam outlet 112, as shown, through a conventional acoustic waveguide 114 (e.g. a ⅛ inch stainless steel rod waveguide, 10 inches long). The transducer 20 may also be directly coupled to the steam generator 102 as shown by the alternative transducer 120. The transmitting transducer 20 driven by a signal from the oscillator 22 (having a frequency distribution such as that illustrated in FIG. 4A) couples a diffuse ultrasonic signal (e.g. at a particular frequency in the range of 50 Khz to 300 Khz in the illustrated embodiment) into the sodium fluid which is transmitted primarily through the fluid to a receiving transducer 24. Use of a diffuse ultrasonic signal in the properly selected frequency range permits interrogation of the entire interior of the steam generator because the signal can pass through and around complex geometries and obstacles such as the tube bundles 110 and baffle plates 109. In the illustrated embodiment, the exact frequency is selected on the basis of the size of the steam generator where the preferred frequency is inversely proportional to the size of the unit.

The transmitted ultrasonic signal is coupled to the receiving transducer 24 by an acoustic wave guide 122 coupled, as shown, to the steam generator tube sheet. The received signal is then coupled from the transducer 24 to the amplifier 26 which amplifies the received signal and couples the amplified signal to the processor 30, as shown. Alternatively, the receiving transducer may be mounted directly on the steam generator as shown by the alternative transducer 124. The signal processor 30 processes the received signal together with a reference signal from the oscillator 22 and a temperature signal from a temperature sensor 28 to determine the void fraction of the sodium fluid. The processor 30 may then output an alarm signal or operational information to an operator.

Figure 3:
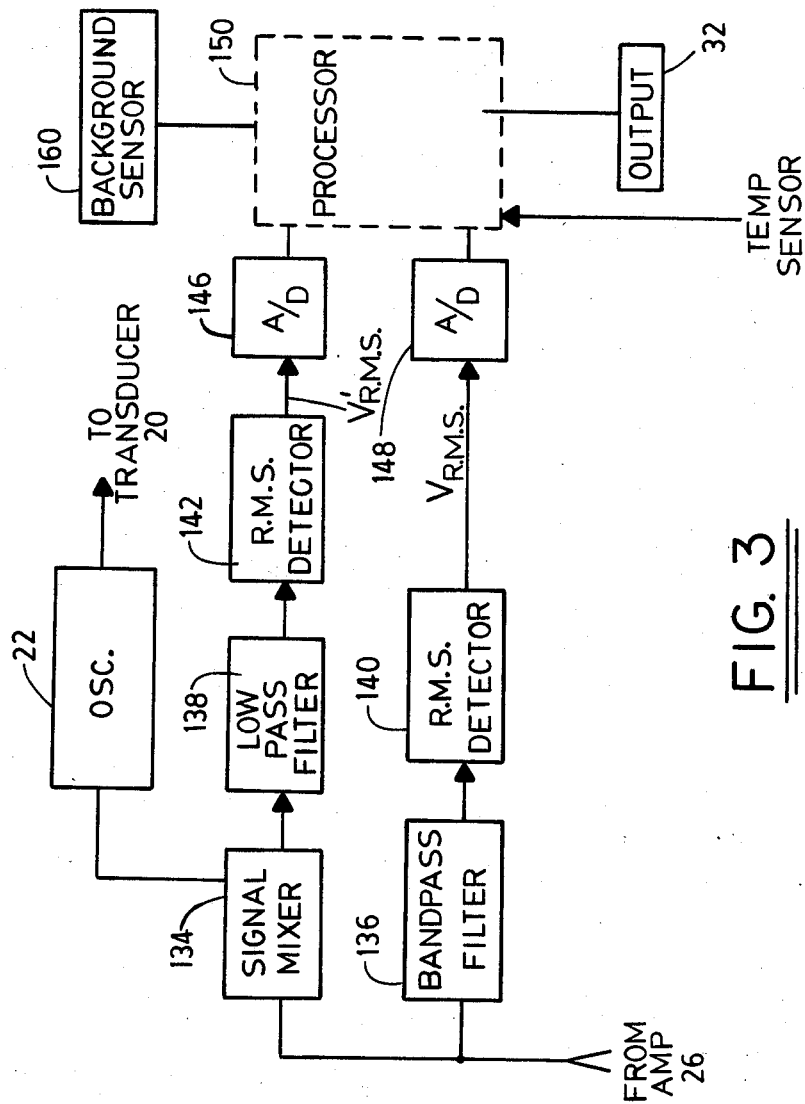
FIG. 3 is detailed block diagram illustrating a specific embodiment of the processor of FIGS. 1 and 2.

One embodiment of the processor 30 is illustrated in the detailed block diagram of FIG. 3. As shown, the oscillator 22 output signal is coupled to an input of a mixer circuit 134. As described hereinbefore, the oscillator 22 generates a narrow band of preselected ultrasonic frequencies such as illustrated in the frequency vs amplitude plot of FIG. 4A. The amplified received signal from the amplifier 26 is also coupled to an input of the mixer 134, as shown, and to the input of a bandpass filter 136. The bandpass filter 136 is a conventional narrow band filter centered on the center frequency $f_0$ of the oscillator 22.

In the illustrated embodiment, the received signal from the receiving transducer 24 will have a general frequency distribution such as that shown in FIG. 4B wherein the narrow band of frequencies centered on the center frequency $f_0$ is attenuated by the presence of voids and wherein additional side-band frequencies have been added due to doppler shift. This signal applied to the bandpass filter 136 results in an output from the filter 136 of only a narrow band of frequencies centered on $f_0$. This signal is coupled, as shown, to the rms detector 140 which produces an output signal $V_{rms}$ which is representative of the root mean square (rms) value of the narrow band of center frequencies. Thus, the output of detector 140 is a signal which represents the energy (i.e. signal strength) of the center frequencies which have been transmitted through the fluid to the receiving transducer 24. This signal may be displayed directly for observation or converted to digital form by an analog to digital converter 148 to permit analysis by processor 150 (e.g. a conventional digital microcomputer). In either case, the output of the detector 140 can be analyzed to determine the deree of attenuation caused by voids or particulates and thereby to determine void fraction.

The amplified received signal from amplifier 26 is also input to the mixer 134 which mixes this signal with the oscillator 22 output signal to produce signal output frequencies $$f = f_0 \pm f_{in} + \text{higher order harmonies}$$

where $f_{in}$ is the frequencies of the signal from the amplifier 26. This output signal from the mixer 134 is filtered by the low pass filter 138 which eliminates the higher frequencies which are of no interest. The resultant output of filter 138 is a signal containing the side-band frequencies of the lower side-band of FIG. 4B. This signal is coupled, as shown, to the rms detector 146 which produces an output signal $V'_{rms}$ representative of the energy (i.e. signal strength) of the side-band signal. This output signal may be displayed directly for observation or converted to digital form by an analog to digital converter 146 to permit analysis by the processor 150. In either case, the output of the detector 142 can be evaluated to determine the amount of side-band energy that has been caused by voids or particulates. This can be used separately or in conjunction with the attenuation of the center frequency to obtain a reliable measure of presence of voids or particulates. A temperature signal from the temperature sensor 28 is coupled to the processor 150 to permit compensation of the center frequency and side-band values for changes in the fluid temperature.

The processor 150 processes the digitized data and provides information to the operator or may activate an automatic control system. The digitized rms values (i.e. $V_{rms}$ and $V'_{rms}$), in one alternative embodiment, may be used to generate a running average over a predetermined time period (e.g. 8 hrs.). This running average is compared to the latest sample of the rms values. Thus, if there is a decrease in $V_{rms}$ which exceeds a minimum value (representative of the minimum change in void fraction from the background level, e.g. approx. 10 millivolts), the processor 150 activates an automatic system to shutdown the reactor or correct the problem, or the processor 150 provides an indication to an operator of the change. The processor 150 may also simply compare the $V_{rms}$ value to a predetermined threshold value obtained empirically for the particular system on which the void/particulate detector is installed and indicate to the operator when the predetermined threshold is exceeded. In another embodiment, when details of the construction of the vessel and material properties of the materials are known, the processor 150 uses $V_{rms}$ to calculate and display a void fraction value ($V_f$) using a relationship $$V_f = (\tfrac{1}{4}V_l)(V_o^2/V_{rms}^2 - 1)\left(\frac{3\gamma p}{\rho}\right)^{\frac{1}{2}}\left[\frac{((\alpha S_i + 8\alpha_l V_l)\delta)^2}{((\delta c(\rho/3\gamma p)^{\frac{1}{2}} - 1)2\pi f)}\right]$$

In a test of the illustrated embodiment of FIG. 2 with the transducers placed approximately 10 meters apart and using the values provided in Table I, a void fraction of $9.1 \times 10^{-11}$ was measured.

TABLE I

| Parameter | Value | Definition |
|---|---|---|
| $V_{rms}/V_o$ | .72 | ratio of received signal voltage over input voltage |
| c | 2577−.536T m/s | velocity of sound in the fluid including temperature dependence (in °C.) |
| $\rho$ | 856 kg/m$^3$ | fluid density |
| p | $2.06 \times 10^5 P_a$ | ambient fluid pressure |
| $\gamma$ | 1.66 | ratio of specific heat at constant pressure over specific heat at constant volume |
| $\alpha$ | $1 \times 10^{-3}$ | absorption coefficient of wall surface |
| $S_i$ | $1.4 \times 10^9$ cm$^2$ | surface area of walls |
| $\alpha_l$ | $(1 \times 10^{-17})$ $(7.3 + 3.95 \times 10^{-2}T)f^2$ cm$^{-1}$ | absorption coefficient of fluid including temp (°C.) and frequency dependence |
| $V_l$ | $8.2 \times 10^5$ cm$^3$ | volume of fluid |
| f | $3.0 \times 10^5$ Hz | frequency of sound |
| $\delta$ | 0.1 | damping constant |
| a | 1.8 cm | radius of bubbles |

Temperature dependence is computed using the temperature sensor signal based upon the above formula or upon empirical data. However, temperature dependence is small compared to the effect of voids to be expected from a typical steam generator leak. This system provides a very sensitive method for measurement of void fraction.

Void and particulate detection using the side-band energy is based upon the principle of Doppler shift. Any obstruction (i.e. particle or void) that has an acoustic impedance different from that of the fluid will reflect some of the ultrasonic energy. As a result of the diffuse nature of the sound field, scattering in many directions will occur. Due to the Doppler effect, the scattered sound wave will be of lower frequency than the incident wave if the obstruction is moving in the same direction as the sound wave scattered and will be of higher frequency if the obstruction is moving in the opposite direction with intermediate frequencies generated at different angles of incidence. As a result, there will be a range of frequencies generated due to doppler shift above and below the center frequency $f_0$ transmitted into the fluid. These side-bands therefore are indicative of the presence of voids and particulates in the fluid. By measuring the magnitude of the side-bands generated an indication of the presence of voids and particulates is obtained. Accordingly, the procesor 150 processes the side-band $V'_{rms}$ value to detect voids or particulates in the same way the center frequency $V_{rms}$ value is processed except that an increase in the $V'_{rms}$ represents an increase in void fraction. Thus, the $V'_{rms}$ value may be converted to void fraction for display to an operator using a relationship $$V_f = \frac{[(A_o V'^2_{rms} V_{Fo})/(V^2_{So}(A_o + 8\alpha_{vo}V_l)]}{[1 - (12V_l/a\delta^2)(V_s/V_{So})^2(V_{Fo}/(A_o + 8\alpha_{vo}V_l)]}$$

where $V_{Fo}$ is background void fraction, $V_{so}$ is background signal level, $V'_{rms}$ is signal level during leak, $A_o = S_i + 8\alpha_l$, and $\alpha_{vo}$ is the absorbtion coefficient for the background void fraction. This measurement determines the void fraction for a particular size bubble. Where the distribution of bubble size is known to be poisson or gaussian, then the single measurement of $V'_{rms}$ can be related to the total void fraction. Alternatively, a minimum increase of $V'_{rms}$ (e.g. 2-3 dB) may be used to trigger an automatic system or alarm. The $V'_{rms}$ value may also be used in conjunction with the $V_{rms}$ value to obtain a more reliable result.

In an alternative embodiment, a background void detection system 160, such as that described in U.S. Pat. No. 4,542,644 issued Sept. 24, 1985 to T. Claytor, et al., is installed on the sodium inlet pipe 104. The background void detection system 160 detects the concentration of voids in the inlet pipe 104 of the steam generator and couples this information to the processor 150. The processor 150 utilizes the background void concentration to correct the void fraction measured in the steam generator so that only voids generated within the steam generator are detected.

Specific embodiments of the apparatus and method for void/particulate detection in a fluid has been described for purposes of illustrating the manner in which the invention may be made and used. It should be understood that implementation of other variations and modification of the invention in its various aspects will be apparent to those skilled in the art, and that the invention is not limited by the specific embodiments described. It is therefore contemplated to cover by the presented invention any and all modifications, variations, or equivalents that fall within the true spirit and scope of the basic underlying principles disclosed and claimed herein.

The embodiments of this invention in which an exclusive property or privilege is claimed are defined as follows:

1. Apparatus for detecting voids and particulates in a fluid within a containing means, the apparatus comprising:
   (a) first transducer means, coupled to a first location on the containing means, for transmitting a diffuse sound field of predetermined frequency into the fluid;
   (b) second transducer means, coupled to a second location on the containing means, for receiving a portion of the transmitted sound field and for generating a signal representative of the received portion of the sound field; and
   (c) signal processing means, coupled to the second transducer, for processing the second transducer signal to determine the presence of voids and particulates responsive to attenuation of the sound field transmitted through fluid.

2. The apparatus of claim 1 wherein the signal processing means further comprises means for processing the second transducer signal to determine the presence of voids and particulates responsive to an increase in side-band energy of the sound field transmitted through the fluid.

3. The apparatus of claim 1 wherein the signal processing means comprises means for determining a void fraction value of the fluid within the containing means responsive to the sound field attenuation.

4. The apparatus of claim 1 wherein the containing means comprises complex geometries.

5. The apparatus of claim 4 wherein the containing means is a steam generator comprising an elongated containing vessel having first and second ends, and wherein the first transducer means is coupled to the steam generator near the first end and the second transducer means is coupled to the steam generator near the second end.

6. The apparatus of claim 5 further comprising background detection means for detecting a background void level in the fluid prior to entry of the field into the steam generator, and wherein the signal processing means further comprises means for correcting the determination of the presence of voids and particulates responsive to attenuation to obtain a void and particulate measure representative of voids and particulates generated within the steam generator.

7. The apparatus of claim 1 wherein at least one of the transducer means is coupled to an acoustic waveguide and the acoustic waveguide is coupled to the containing means.

8. The apparatus of claim 1 further comprising a temperature sensing means for sensing the temperature of the fluid and for coupling a signal representative of the fluid temperature to the signal processing means.

9. The apparatus of claim 1 wherein the predetermined frequency is less than 500 khz.

10. The apparatus of claim 1 wherein the containing means comprises a pipe through which the fluid flows and wherein the first transducer transmits a diffuse sound field in an axial direction into the fluid and wherein the second transducer is axially displaced from the first transducer.

11. The apparatus of claim 1 wherein the signal processing means comprises means for bandpass filtering the signal representative of the received portion of the sound signal and means for generating a center frequency signal representative of the signal strength of the filtered signal.

12. The apparatus of claim 11 wherein the signal processing means further comprises means for isolating at least one side-band of the signal representative of the received portion of the sound field and means for generating a control signal representative of the signal strength of a side-band isolated thereby.

13. The apparatus of claim 12 wherein the signal processing means further comprises processing means for processing at least one of the center frequency signal and the control signal to detect the presence of voids and particulates, and for generating output signals responsive to at least one of the center frequency signal and control signal.

14. The apparatus of claim 1 wherein the predetermined frequency is a resonant frequency with respect to some of the voids.

15. A method of detecting voids and particulates in fluid within a containing vessel, comprising the steps of:
(a) transmitting diffuse acoustic energy into the fluid;
(b) detecting the amount of absorption of the diffuse acoustic energy.

16. The method of claim 15 wherein the diffuse acoustic energy is an ultrasonic signal transmitted by a transducer.

17. The method of claim 16 wherein the fluid flows in a predetermined direction and wherein the ultrasonic signal is transmitted along the axis of flow at a preselected location and is detected at a different location along the axis of flow.

18. The method of claim 16 further comprising the steps of sensing the temperature of the fluid and compensating for temperature dependent changes in absorption of the diffuse acoustic energy.

19. The method of claim 15 further comprising the steps of detecting the amount of acoustic side-band energy produced by voids and particulates within the fluid and determining the presence of voids and particulates responsive to the amount of acoustic sideband energy.

20. The method of claim 15 further comprising the step of determining the void fraction within the fluid responsive to the detected amount of absorption of the diffuse acoustic energy.

21. Apparatus for detecting voids and particulates in a fluid within a containing means, the apparatus comprising:
(a) first transducer means, coupled to a first location on the containing means, for transmitting a diffuse sound field of predetermined frequency into the fluid;
(b) second transducer means, coupled to a second location on the containing means, for receiving a portion of the transmitted sound field and for generating a signal representative of the received portion of the sound field; and
(c) signal processing means, coupled to the second transducer, for processing the second transducer signal to determine the presence of voids and particulates responsive to attenuation of the sound field transmitted through fluid and including means for bandpass filtering the signal representative of the received portion of the sound signal, means for generating a center frequency signal representative of the signal strength of the filtered signal, means for isolating at least one sideband of the signal representative of the received portion of the sound field and means for generating a control signal representative of the signal strength of a side-band isolated thereby.

22. The apparatus of claim 21 wherein the signal processing means further comprises processing means for processing at least one of the center frequency signal and the control signal to detect the presence of voids and particulates, and for generating output signals responsive to at least one of the center frequency signal and control signal.

23. A method of detecting voids and particulates in fluid within a containing vessel, comprising the steps of:
(a) transmitting diffuse acoustic energy into the fluid;
(b) detecting the amount of absorption of the diffuse acoustic energy; and
(c) detecting the amount of acoustic side-band energy produced by voids and particulates within the fluid and determining the presence of voids and particulates responsive to the amount of acoustic side-band energy.

* * * * *